United States Patent
Van Hoesel (10) Patent No.: US 7,310,558 B2
(45) Date of Patent: Dec. 18, 2007

(54) PEAK-DERIVED TIMING STIMULATION STRATEGY FOR A MULTI-CHANNEL COCHLEAR IMPLANT

(75) Inventor: Richard Van Hoesel, East Brunswick (AU)

(73) Assignee: Hearworks PTY, Limited, Victoria (AU)

( * ) Notice: Subject to any disclaimer, the term of this patent is extended or adjusted under 35 U.S.C. 154(b) by 630 days.

(21) Appl. No.: 10/478,675

(22) PCT Filed: May 24, 2002

(86) PCT No.: PCT/AU02/00660

§ 371 (c)(1),
(2), (4) Date: Apr. 15, 2004

(87) PCT Pub. No.: WO02/096153

PCT Pub. Date: Nov. 28, 2002

(65) Prior Publication Data

US 2004/0172101 A1 Sep. 2, 2004

(30) Foreign Application Priority Data

May 24, 2001 (AU) .................................... PR5234

(51) Int. Cl.
*A61N 1/36* (2006.01)

(52) U.S. Cl. ........................................................ 607/57

(58) Field of Classification Search ............ 607/55–57, 607/136–137
See application file for complete search history.

(56) References Cited

U.S. PATENT DOCUMENTS 6,198,971 B1 * 3/2001 Leysieffer .................... 607/55

FOREIGN PATENT DOCUMENTS

| BE | WO0119304 A1 * | 3/2001 |
| WO | WO99/65276 | 12/1999 |
| WO | WO 01/03622 | 1/2001 |
| WO | WO 01/99470 | 12/2001 |

* cited by examiner

*Primary Examiner*—George R. Evanisko
*Assistant Examiner*—Rex Holmes
(74) *Attorney, Agent, or Firm*—Connolly Bove Lodge & Hutz, LLP (57) ABSTRACT

A binaural cochlear implant system, including two intracochlear implants adapted for implantation in the cochleas of a user, each cochlear implant utilising a speech processing strategy wherein the electrical stimuli are matched to the relative timing of the relevant audio signals as detected at each ear, such that the interaural time delays between the audio signals at each ear are substantially preserved in electrical stimuli at each ear.

The processing strategy comprises band pass filtering the audio signal, determining the peaks in, and intensity of, each band, prioritising and placing each peak in a buffer in time slots corresponding to the relative timing of each peak. The buffer output forms the basis for stimulus instructions.

12 Claims, 7 Drawing Sheets

CALCPEAKS ROUTINE

```
function [peak2] = calcpeaks(y,N)
lastpeak=1;
peak2=zeros(1,N);
canreinstate=100000;     % some # > buffer leng = can't reinstate any
reinstateval=0;
for i=2:N-1
    if (y(i)>0) & ((y(i-1)<y(i)))      % threshold now set > 0 (noise
                                       % floor 1/2000)
        if (y(i+1)<y(i))               % found another peak
            if i-lastpeak<10
                if y(i) > y(lastpeak)  % new larger peak -> clear prev.
                                       % (maybe reinstate one before that)
                    peak2(lastpeak)=0;
                    peak2(i)=y(i);
                    if i-canreinstate > 10
                        peak2(canreinstate)=y(canreinstate);
                        canreinstate=i;
                    end
                    lastpeak=i;
                end
            else
                peak2(i)=y(i);
                lastpeak=i;
                canreinstate=lastpeak;  % have timed out reinstate option
                                        % (only relevant to close peaks)
            end
        end
    end
end
peak2(N-1)=0;
peak2(N)=0;
```

Fig. 3

```
% N=length of input signal peak=zeros(1,N);        % THIS IS THE TOTAL STIM BUFFER
shift1=zeros(1,10);
shift2=zeros(1,10);
peakchan=zeros(1,N);    % listing of channel corresponding to each peak
peakoff=zeros(1,N);     % listing of peak offseet from where it should
                        % have been (for STATS only)

for ch=1:10     % low to high band priority
                % lowest channel contributes to total buffer
                % fisrt, so has no clashes, etc.
switch ch
case 1, y=y1;
```

*Fig. 4*

```
    case 2, y=y2;
    case 3, y=y3;
    case 4, y=y4;
    case 5, y=y5;
    case 6, y=y6;
    case 7, y=y7;
    case 8, y=y8;
    case 9, y=y9;
    case 10, y=y10;
end peak2=calcpeaks(y,N);

for i=1:N                            % scan buffer one sample at a time
    if peak2(i) > 0 & peak(i) > 0  % CLASH
        if ch < 5 & peak2(i)>=(2*peak(i))   % in T-sens chans, preserve
                                            % place of largest @ clash
            if peak(i+1) ==0
                peak(i+1)=peak(i);    %shuffle old value as clashed now
                peak(i)=peak2(i);     %move new peak into "old" buffer"
                peak2(i)=0;
                peakchan(i+1)=peakchan(i);
                peakchan(i)=ch;
                peakoff(i+1)=peakoff(i)+1;
                peakoff(i)=0;
            elseif peak(i-1)==0
                peak(i-1)=peak(i);    %shuffle old value as clashed now
                peak(i)=peak2(i);     %move new peak into "old" buffer"
                peak2(i)=0;
                peakchan(i-1)=peakchan(i);
                peakchan(i)=ch;
                peakoff(i+1)=peakoff(i)-1;
                peakoff(i)=0;
            elseif peak(i+2)==0
                peak(i+2)=peak(i);    %shuffle old value as clashed now
                peak(i)=peak2(i);     %move new peak into "old" buffer"
                peak2(i)=0;
                peakchan(i+2)=peakchan(i);
                peakchan(i)=ch;
                peakoff(i+2)=peakoff(i)+2;
                peakoff(i)=0;
            elseif peak(i-2)==0
                peak(i-2)=peak(i);    %shuffle old value as clashed now
                peak(i)=peak2(i);     %move new peak into "old" buffer"
                peak2(i)=0;
                peakchan(i-2)=peakchan(i);
                peakchan(i)=ch;
                peakoff(i-2)=peakoff(i)-2;
                peakoff(i)=0;
            else
                peak(i)=peak2(i);     % new peak takes its place
                peak2(i)=0;
                unresolved(ch)=unresolved(ch)+1;
            end
        else                          % shift new pulse
                                      % (keep old one in place)
            if peak(i+1)==0
                peak2(i+1)=peak2(i);
                peak2(i)=0;
                peakoff(i+1)=1;
                peakchan(i+1)=ch;
```

*Fig. 4a*

```
            elseif peak(i-1)==0
                peak2(i-1)=peak2(i);
                peak2(i)=0;
                peakoff(i-1)=-1;
                peakchan(i-1)=ch;
            elseif peak(i+2)==0
                peak2(i+2)=peak2(i);
                peak2(i)=0;
                peakoff(i+2)=2;
                peakchan(i+2)=ch;
            elseif peak(i-2)==0
                peak2(i-2)=peak2(i);
                peak2(i)=0;
                peakoff(i-2)=-2;
                peakchan(i-2)=ch;
            else
                peak2(i)=0;
            end
          end
      end
   end
   for i=1:N
       if peak2(i)>0 & peakoff(i)==0   % no clash case statistics
           peakchan(i)=ch;
       end
   end
   peak=peak+peak2;
end end
```

PEAK-DERIVED TIMING STIMULATION STRATEGY FOR A MULTI-CHANNEL COCHLEAR IMPLANT

CROSS REFERENCE TO RELATED APPLICATIONS

This application is a national stage application of PCT/AU02/00660, entitled "A Peak-Derived Timing Stimulation Strategy For a Multi-Channel Cochlear Implant," filed on May 24, 2002, which claims the priority of Australian Provisional Application No. 5234, entitled "A Peak-Synchronous Timing Stimulation Strategy For a Multi-Channel Cochlear Implant," filed May 24, 2001, the entire disclosure and contents of which is hereby incorporated by reference.

TECHNICAL FIELD

The present invention relates to an improved method for generating electrical stimuli for application to the neural structures of a cochlea, and to devices implementing such strategies.

BACKGROUND ART

Cochlear implant systems generally operate by receiving a sound signal, processing the received signal in order to extract information to be used as the basis for stimuli, and then generating the required stimuli for delivery by an intra-cochlear electrode array. The speech processing strategy is the process used to determine which information extracted from the sound signal is to be used as the basis for stimulation, and some of the characteristics of the stimuli to be applied.

There have been a number of speech processing strategies introduced with multi-channel cochlear implants that have used rates of stimulation synchronised to a speakers fundamental frequency. Due in the main to power considerations, such strategies only selected a few electrodes and stimulation occurred at a low F0 (fundamental frequency or repetition) rate.

Essentially, these strategies employed a filter channel dedicated to extracting the voice pitch of the speech signal. The periodicity of the voice pitch was used to set the stimulation periodicity for two or three electrodes. A second and possibly third channel was analysed to determine the frequency (periodicity) and amplitude (energy) within a frequency band. The periodicity extracted from the second and/or third filters was used to select which electrode was to be stimulated for the second and third channel. The periodicity of stimulation on these channels was the same for all channels and was determined from the periodicity of the output channel from the F0 filter. In each case the amplitude of the output signal from the corresponding filter determines the amplitude of the stimulation in a given channel.

As technology advances have allowed, higher stimulation rates have become progressively available through the 1990's and the F0 synchronous stimulation has been replaced with "high" rate stimulation strategies such as SPEAK and CIS which typically stimulate at a rate in the range of 250-3000 Hz per electrode.

The SPEAK strategy, which is described in U.S. Pat. No. 5,597,380 (and which is implemented in a number of speech processors produced by Cochlear Limited) employs a larger number of analysis filters and stimulates more electrodes each analysis period than the F0 synchronous strategy. During each analysis period, the SPEAK strategy interrogates the output of each one of an array of spectral analysis filters and stimulation is applied only to those electrodes corresponding tonotopically to the selected filters with the largest amplitude. In this case the frequency of stimulation of each individual electrode is variable depending upon the amplitude of the signals corresponding to each electrode.

The CIS strategy is described in U.S. Pat. No. 4,207,441. In this strategy there are n electrodes each coupled to one of n filters. Each electrode is stimulated once per analysis period, with an intensity corresponding to the amplitude of the corresponding filter channel. In this strategy the analysis period is predetermined and hence the frequency of stimulation for each electrode is more or less fixed.

More recently in PCT/AU00/00838 by the present applicant, there is described a strategy which extracts stimulation rates from the input signal and provides for stimulation of different electrodes at different rates (the multi rate scheme). The multi rate scheme sets the stimulation rate and amplitude for a selected electrode according to measurements of the signal characteristics in the corresponding filter band and also describes an arbitration scheme to deal with conflicting times of stimulation.

The multi rate scheme estimates the rate of stimulation in each band by measuring intervals between positive zero crossings of the filtered signal without regard to where in absolute time the zero crossings occur. This is intended to provide periodicity information to the user. In the multi rate scheme the overall rate is limited by smoothing of the rate estimates so that the absolute timing of the events is not captured.

A further issue that is not addressed by prior speech processing strategies is that of interaural time delays for binaural listening. With the strategies designed so far, filterbank methods have been used which discard the carrier phase in each band, and preserve (at best) the envelope modulations in the band. However, for normal hearing, it is often the case that for low frequencies at least, the carrier phase differences between the two ears are an important cue. Also, with fixed sampling rate strategies such as SPEAK and CIS, asynchronous sampling even of the envelope at the two ears can introduce inconsistent level cues between the two ears.

There have been a number of studies undertaken in the area of benefits associated with binaural listening, for example:

Bronkhorst, A. W., and Plomp, R., 1988, The effect of head-induced interaural time and level differences on speech intelligibility in noise, *Journal of the Acoustical Society of America*, 83, 1508-1516.

Bronkhorst, A. W., and Plomp, R., 1989, Binaural speech intelligibility in noise for hearing-impaired listeners, *Journal of the Acoustical Society of America*, 86, 1374-1383.

Carhart, R.,1965, Monaural and binaural discrimination against competing sentences, *International Audiology*, 4, 5-10.

Dirks, D. D. and Wilson, R. H., 1969, The effect of spatially separated sound sources on speech intelligibility, *Journal of Speech and Hearing Research*, 12, 5-38.

Hausler, R., Colburn, S., and Marr, E., 1983, Sound Localization in Subjects with Impaired Hearing, *Acta Otolatyngologica*, Supplement 400.

Hawley, M. L., Litovsky, R. Y., Colburn, H. S., 1999, Speech Intelligibility and localization in a multi-source environment, *Journal of the Acoustical Society of America*, 105, 3564-3448.

Licklider, J. C. R., 1948, The influence of interaural phase upon the masking of speech by white noise", *Journal of the Acoustical Society of America*, 20, 150-159.

MacKeith, N. W, and Coles, R. R., 1971, Binaural advantages in hearing of speech, *Journal of Latyngology and Otology*, 85, 213-232.

Peissig, J. and Kollmeier., B., 1997, Directivity of binaural noise reduction in spatial multiple noise-source arrangements for normal hearing and impaired listeners, *Journal of the Acoustical Society of America*, 105, 1660-1670

Rayleigh, L., 1907, On our perception of sound direction, *Philosophical Magazine*, 13, 214-232.

Sayers, B. M., 1964, Acoustic-image lateralization judgments with binaural tones, *Journal of the Acoustical Society of America*, 36, 923-926.

Searle, C. L., Braida, L. D., Davis, M. F., and Colburn, H. S., 1976, Model for auditory localization., *Journal of the Acoustical Society of America*, 60, 1164-1175.

Wightman, F., and Kistler, D. J., 1992, The dominant role of low-frequency interaural time differences in sound localization, *Journal of the Acoustical Society of America*, 91, 1648-1661.

It is accepted that listening with two ears rather than one, for normal listeners, allows improved speech intelligibility in noise as well as the ability to better determine sound direction. Studies with both normal hearing and hearing impaired listeners have suggested that the binaural intelligibility level difference (BILD) is a function of both interaural level differences (ILD) and interaural time delays (ITD). Similarly, localisation in the horizontal plane has been shown to be a function primarily dependent on ILD and ITD cues at the two ears.

It is an object of the present invention to provide a speech processing strategy that provides improved temporal information for a cochlear implant user.

SUMMARY OF THE INVENTION

The present invention provides, in broad terms, a speech processing strategy in which the time of stimulus for a given electrode is substantially synchronised to the temporal peak in the filter output corresponding to that electrode. As a consequence, the timing information for the corresponding sound signal—and not merely the amplitude or periodicity of that signal—is presented to the user.

In essence the present invention concentrates on utilising the occurrence of peaks in the band-pass filtered signal of the detected sound to dictate the stimulation applied to the cochlea. By concentrating on the occurrence of peaks in the band-pass filtered signal the time of stimulation can be set to stimulate at the time positive peaks occur in each band and ensures improved temporal accuracy of the stimulation by ensuring that the amplitude of the detected peaks is presented at the appropriate time. This enables the temporal information in the signal to be better preserved providing the user with improved real time stimulation.

As a consequence of the approach taken, the present invention may better convey information about a multiplicity of signals in each filterband. This is in contrast to most sound processing schemes that represent information from each band with a single stimulation rate, including the multi rate strategy that averages zero crossing information from all signals in the band. The potential advantage is that the listener may be able to better separate harmonics from multiple sound sources, even though the components are mixed together in each filterband. This could assist in for example in separating simultaneous speakers.

In a practical implementation with non-simultaneous stimulation, it is important that all bands can be stimulated non-simultaneously and stay within the overall rate limitations of existing cochlear implant devices by limiting the stimulation rate on each electrode. In a preferred implementation of the present invention, this is done within each band by specifying a minimal allowed separation of peaks. If the peaks in a band are closer than the minimum interval allowed, only the largest peak is preserved.

This method of limitation ensures that stimulation of preserved peaks remains in synchrony with the input audio signal, in contrast to the approach of saturating the stimulation rate at some fixed value as is the case with many other strategies.

In order to avoid simultaneous stimulation on multiple channels for non-simultaneous devices, an arbitration scheme is also required in the event that peaks occur simultaneously in two or more bands. The arbitration scheme according to one implementation of the current invention resolves such clashes in a manner that minimizes temporal distortion in the frequency bands where listeners are more sensitive to fine temporal information, and in particular interaural time delays (ITDs) in the fine-timing.

More specifically, the preferred implementation of the current invention uses a scheme whereby in the low frequency region, for example up to about 1500 Hz, priority is given to stimulations from low frequency to high frequency unless the peak in the higher frequency band is a specified ratio larger than the lower band, for example twice as large. For frequencies above about 1500 Hz, priority is given simply from low to high frequency peaks. When clashes occur, lower priority peaks are shifted either forwards or backwards in time to the nearest available stimulation interval. Only when all nearby times are occupied with previously assigned peaks of higher priority, and the time shift required exceeds a specified threshold, does the scheme delete the peak and not include it for stimulation. By carefully setting the number of bands and setting appropriate thresholds, peaks in lower frequency bands can be preserved very accurately and even for the higher bands (where listeners are not so sensitive to temporal cues) peaks should rarely be deleted altogether. It should be appreciated that if devices capable of simultaneous stimulation are used instead, the arbitration scheme can be omitted from the invention without complication.

The present invention can be of benefit to single cochlear implant users and also has specific application to binaural cochlear implant patients having a cochlear implant in each ear. In the binaural case the invention assists in accurately preserving time-of-arrival differences between both ears and in such cases the strategy of the current invention would need to be applied to each ear.

From the limited number of publications regarding bilateral implant users to date, it is clear that both improved ability to determine sound direction in the horizontal plane and understanding speech in spatial separated noise are likely to result for implantees using two devices as opposed to one (van Hoesel and Clark, 1999, "Speech results with a bilateral multi-channel cochlear implant for spatially separated signal and noise", Aust. J. Audiol, 21, 23-28; van Hoesel, Ramsden and O'Driscoll, 2002, "Sound-direction identification, interaural time delay discrimination and speech intelligibility advantages in noise for a bilateral cochlear implant user", Ear Hear., April 2002; van Hoesel and Tyler, "Speech perception, localization and lateralization with bilateral cochlear-implant users"—submitted to J.Acoust.Soc.Am., 2002). However, a good deal of these benefits at present seem to be derived from interaural level differences, and it is at this stage not clear how much additional benefit can be derived from interaural timing information. Normal hearing listeners on the other hand clearly benefit from both ILDs and ITDs. The potential contribution from ITDs with cochlear implant users depends both on the sound-coding strategy's ability to preserve the information in the translation from acoustic to electrical stimulation, as well as the listener's ability to make use of the information in the electrical pulses. The present invention specifically addresses the former of these.

Although early studies by van Hoesel and Clark (1997) showed that some bilateral implant users have very poor ITD sensitivity (around 0.5 ms or more), the more recent study by van Hoesel and Tyler (submitted 2002) has shown that others demonstrated moderately good ITD sensitivity around 100-150 µs or occasionally better. Although this is not as good as normal hearing, delays of this magnitude are available from signals in everyday scenarios when they are more than about 10 degrees from the median. The same study also shows that, for unmodulated pulse-trains, this sensitivity becomes much worse at stimulation rates beyond a few hundred Hz. For 800 pps stimulation rates, the studies showed that ITD sensitivity could, however, be substantially improved by applying a 50 Hz modulation. In that case both 'carrier' and envelope were simultaneously delayed in one ear. Early indications are in fact that if the carrier (i.e. stimulus fine timing) is held fixed and only the envelope is delayed in one ear, ITD sensitivity is comparable to delaying the entire stimulus. This would be expected from the poor ITD sensitivity to high rate unmodulated pulse-trains. The implication is that even with existing fixed-rate strategies listeners should demonstrate moderately good ITD sensitivity for envelopes of signals. However, in the normal hearing case envelope information is important for high frequencies, whereas for lower frequencies, fine timing of the signals becomes more important. In fact the normal hearing system is considerably more sensitive to ITDs in fine-timing, particularly between 800 and 1000 Hz than it is to envelope ITDs of high frequency signals. The present invention aims to address this issue by better coding fine timing ITDs in addition to the envelope ITDs.

On a related note, it is worth observing that monaural pitch percepts saturate for electrical pulse-rates above a few hundred Hz for many subjects, and that this may be indicative of the auditory system's inability to convey temporal information beyond those rates. This may be why in bilateral ITD studies to date subjects have shown poor ITD sensitivity for signals with temporal variations faster than a few hundred Hz. This result means that the present invention for now may be more effective than existing approaches only for signals satisfying the low temporal-rate criterion.

A number of details comparing the present invention with previous approaches follow.

The multi rate scheme estimates the rate of stimulation in each band by measuring intervals between positive zero crossings of the filtered signal without regard to where in absolute time the zero crossings occur. As the previous multi rate scheme also suggested smoothing of the rate estimate, absolute times of the events are further lost. The current invention does not estimate rates but rather stimulates on positive peaks in the signal, at the time they actually occur (allowing for a fixed processing delay).

The preferred implementation of the present invention also uses the peak magnitudes presented at the appropriate time to ensure that the overall stimulation envelope for any band is accurate. It will be appreciated that other energy measures related to the time of the peak could be used, for example a windowed rms value around the peak. The peaks of either the envelope or carrier could be used. Such implementations are included within the term peak magnitude as used in the specification and claims. The important issue is that the measure is related to the time of the peak. In the multi rate application, the placement of peak magnitude pulses at zero crossings would distort temporal information since the signal actually has zero energy at the zero crossing time and because relative timing of peaks and zero-crossings doesn't remain constant for arbitrary signals. The current invention therefore improves the temporal information by presenting peak magnitude pulses at the time they actually occur.

The preferred implementation of the present invention also differs from the previous multi rate strategy in the number of electrical pulses for the same signal segment delivered by each of the schemes. As the multi rate scheme uses one electrical pulse per measured rate interval (positive going zero crossing derived) and the new scheme uses positive peaks, the number of zero crossings and positive peaks are not the same for most arbitrary signals, so that a different number of electrical pulses is delivered per signal segment.

The preferred implementation of the present invention also provides a novel and inventive rate limitation method compared to the multi rate strategy. In the multi rate strategy the overall rate is limited by smoothing of the rate estimates which as previously mentioned loses the absolute timing of the events, and for high rates in fact totally decorrelates zero crossing rates with stimulus rates. The preferred implementation of the present invention applies a specified limit on the allowable spacing between peaks in a band to allow temporal intervals up to about 700 microseconds to span frequencies where temporal discrimination is highest, and also corresponds approximately with auditory nerve absolute refractory times.

The preferred implementation of the present invention also differs from the previous multi rate scheme by applying a novel and inventive method of handling clashes between simultaneous stimulation peaks in multiple bands. The multi rate scheme applied an ordering system to the stimulations according to amplitude and moved lower amplitude bands up to 5 stimulation intervals later in time. The preferred implementation of the present invention orders the stimulations according to frequency, with additional amplitude considerations in the lower frequency bands. This new method has been implemented because of observations in the literature that the temporal sensitivity, and in particular binaural sensitivity is best below 1500 Hz. See for example Klump & Eady, 1956, "Some measurements of interaural time difference thresholds", JASA 28, pp859-860. In the preferred implementation of the present invention lower priority pulses are shifted up to 2 stimulation intervals earlier or later in time.

BRIEF DESCRIPTION OF THE DRAWINGS

A preferred implementation of the present invention will now be described with reference to the accompanying figures, in which.

DETAILED DESCRIPTION

Figure 1:
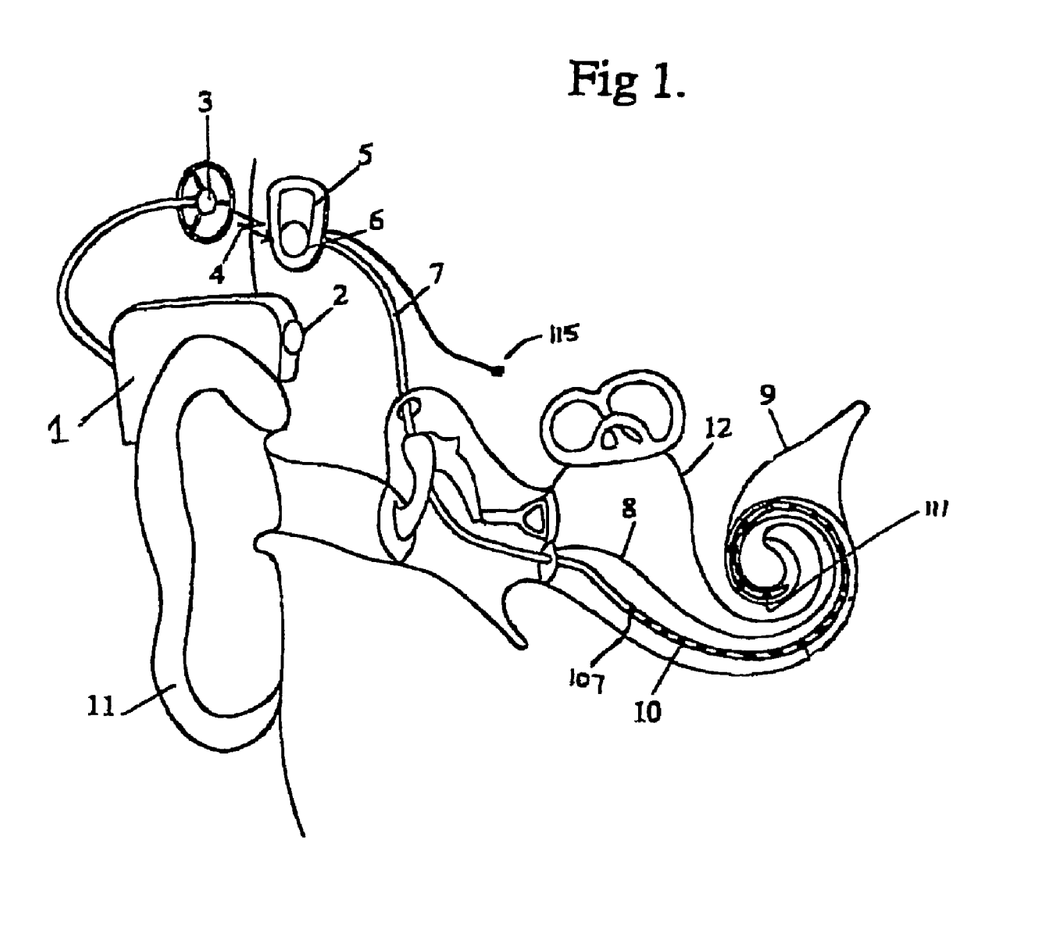
FIG. 1 depicts a typical cochlear implant device.

With reference to FIG. 1, a typical cochlear implant is shown which consists of an external component including a speech processor 1, and an internal component including an implanted receiver and stimulator unit 6 and an intracochlear array 10. The external component further includes a microphone 2 which is shown integral with the speech processor 1. In this illustration the speech processor is arranged so that it can fit behind the ear with the microphone integral therewith. Alternative versions are also envisaged whereby the speech processor is worn on the body and separately attached to the microphone, and also where the speech processor and microphone are implanted in the patient. The present invention is applicable to all these alternatives and it should also be appreciated that a binaural version of this strategy is also possible and would generally involve two independent units with a microphone behind each ear.

In such a device or devices, ambient sounds are detected by a microphone 2 and a transduced signal is thereby generated, representative of the ambient sound. The processor unit 1 then processes this transduced signal according to one of a number of strategies (the strategy of the current invention will be explained in more detail below) and based on this processing, stimulation currents are applied between the electrodes of intracochlear array 10. For example, in "monopolar" mode stimulation, stimulation currents may be caused to flow between an electrode of the electrode array 10 and an extracochlear electrode 115. Nervous discharges elicited in the basilar membrane 8 are conveyed to the central nervous system of the wearer by the auditory nerve 9.

In the event that the stimulation current flows between an apical electrode such as electrode 111 and extracochlear electrode 115 then a lower pitched hearing sensation will be perceived by the wearer of the prosthesis than will be the case if stimulation current flows between basal electrode 107 and extracochlear electrode 115 because of the tonotopic arrangement of the cochlea.

The present invention will now be described with reference to a specific implementation. However it will be appreciated that the present invention can be implemented in various ways, with suitable modifications to suit the cochlear implant system in question.

Figure 2:
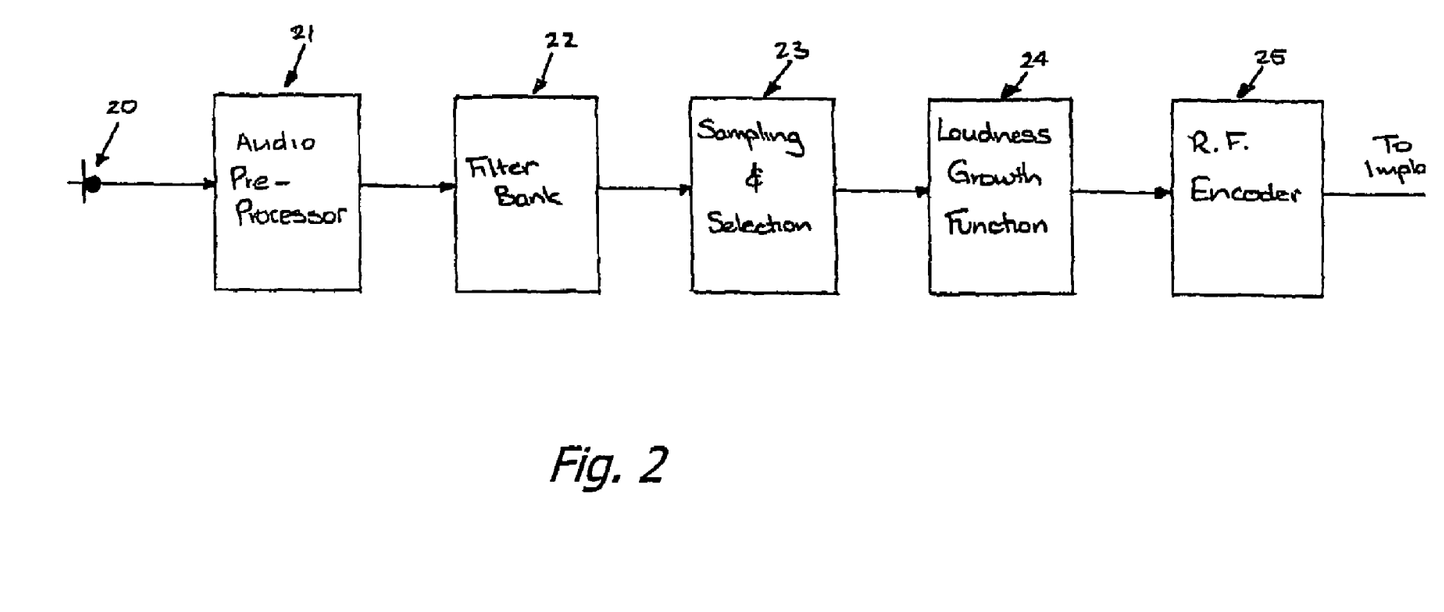
FIG. 2 depicts a block diagram of the signal flow in the speech processing strategy according to an implementation of the present invention.

With reference to FIG. 2, there is depicted a block diagram of the overall signal flow from the microphone to the implant for the current invention. The basic function of a speech processor is to take an audio signal from a microphone 20 and to process it according to a particular speech coding strategy to produce a signal, typically on an RF signal, that contains stimulation information for an implant.

As previously mentioned, ambient sounds are detected by the microphone 20 and a transduced signal is thereby generated, representative of the ambient sound. The audio pre-processor 21 essentially amplifies the very low signal received from the microphone to a level which can be easily handled by the rest of the signal processing system. If the sounds are very soft a large amount of amplification (gain) may be needed, and if the sounds are loud less gain is needed. The amount of gain applied to the sound is controlled by the user via their sensitivity control, in conjunction with any automatic gain control or automatic sensitivity control provided for in the system. As the operation of a audio pre-processor is well known in the art and not important to the understanding of the current invention, no further description of this feature will be provided.

The next stage in the signal processing flow is the filterbank 22. The filterbank essentially consists of a set of band-pass filters covering the input frequency range of the system. The frequency bounds are based on critical bands, roughly linearly spaced below 1000 Hz and logarithmically spaced above 1000 Hz. Each filter is allocated to one channel, so the number of filters is equal to the number of channels. A band-pass filter allows signals in one band of frequencies to pass through whilst blocking other frequencies. It is desirable that the number of filter bands (channels) be programmable due to the fact that different strategies use different numbers of filters and the number of available channels depends on the mode of stimulation, eg monopolor, common ground etc. A filterbank is usually visualised as operating continuously providing a set of N parallel, continuous output signals.

The next stage in the signal processing is Sampling and Selection 23. In general during this stage the speech processing strategy employed samples each of the filterbank outputs and determines a sequence of stimulus frames. It is this sampling and selection process with which the current invention is concerned and this will be explained in more detail below.

The next stage of the signal processing is the Loudness Growth Function (LGF) 24 which is essentially related to amplitude mapping. This stage takes the information from Sampling and selection block 23 and maps it onto the patients electrode array. For each stimulation selected it selects the electrode assigned to that frequency and sets the amplitude of the stimulation to a level that is between the users threshold and comfort levels to represent the loudness of that frequency component. In modern systems, the mapping, threshold and comfort levels are specific to the particular user, and are individually determined either by an automatic process, or by a process of audiological measurements.

The final stage of the signal processing is the R.F. Encoder 25 which takes the information of the processed signal that is to be presented to the patients electrode array and converts it to a code which can be transmitted to the implanted receiver/stimulator for subsequent stimulation by the electrodes of the implanted electrode array. It will be understood that the latter process will differ somewhat in, for example, a totally implanted or hard wired implementation.

The strategy of the preferred implementation of the present invention to be applied at the Sampling and Selection stage 23 will be described in relation to a simple, unilateral version of this scheme having ten IIR filter bands, each about 2-3 critical bands wide and in total spanning approximately 200-7000 Hz which are used to derive stimulation parameters for ten fixed electrodes. The filters of the described system have been designed to give a composite ripple of less than 2 dB and have 18 dB roll-offs beyond the cut-off frequencies. The sampling rate in the described code is about 16000 Hz. It is to be appreciated that the above parameters have been selected to assist in the description of the current invention and that variations to these parameters and to this type of implementation can be made within the scope of the invention.

Figure 3:
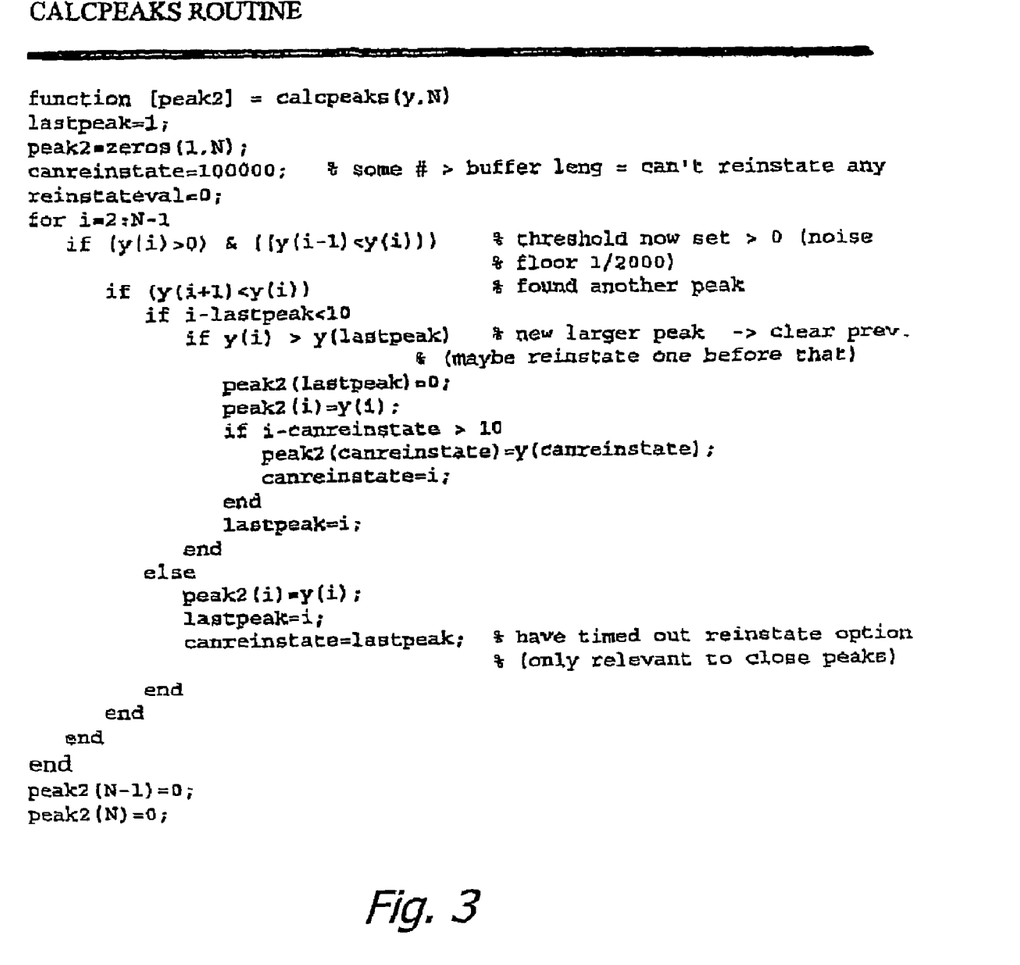
FIG. 3 depicts the code associated with calculating the peaks of the signal according to one implementation of the invention.

Following the audio pre-processing stage, the signal is then passed through a filterbank consisting of 10 IIR filter bands which splits the signal into 10 bands according to predesigned frequency boundaries. The bandpass filtered signal from each of the bandpass filters is then analysed to calculate the peaks in a given band and the band pass signal is then replaced with the peaks it contains. This is done according to the code of FIG. 3 referred to as the CAL-CPEAKS routine. This routine further introduces a 'canreinstate' variable that keeps track of any peaks that have been temporarily nulled because they were too close to a neighbouring peak. This occurs because the current invention does not employ a smoothing of the rate estimates to limit the overall rate but rather applies a specified limit on the allowable spacing between peaks in a band. This is chosen to allow temporal intervals up to about 700 microseconds to span frequencies where temporal discrimination is best and also corresponds approximately with auditory neural refractory times. By keeping track of this variable the peak can be reinstated should the neighbouring peak itself become nulled.

Figure 4:
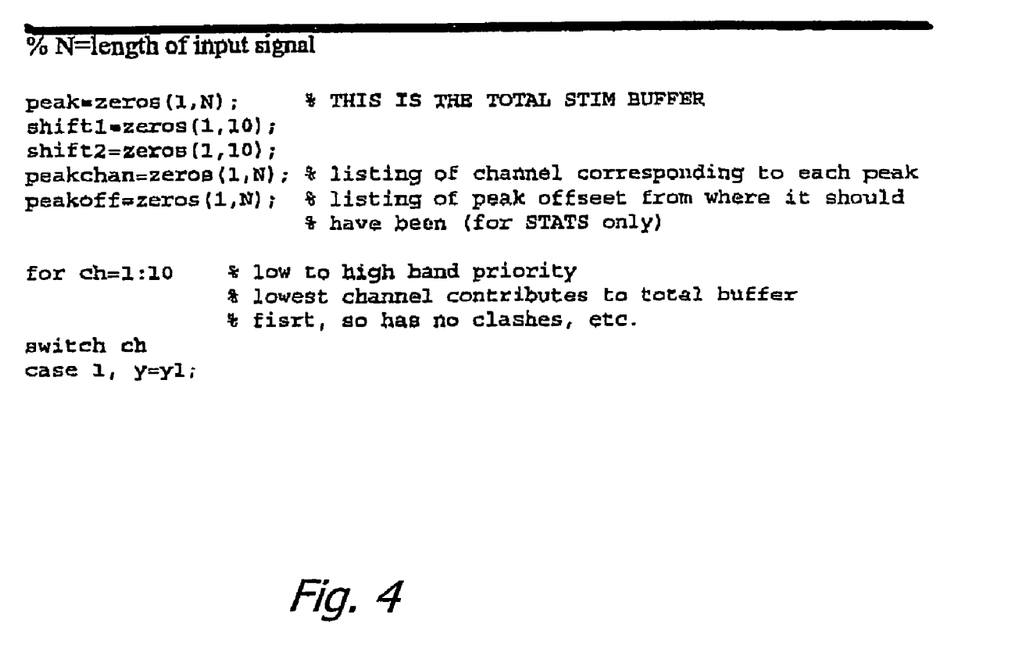
FIG. 4 depicts the main code according to one implementation of the invention including the proposed arbitration method.
Figure 4A:
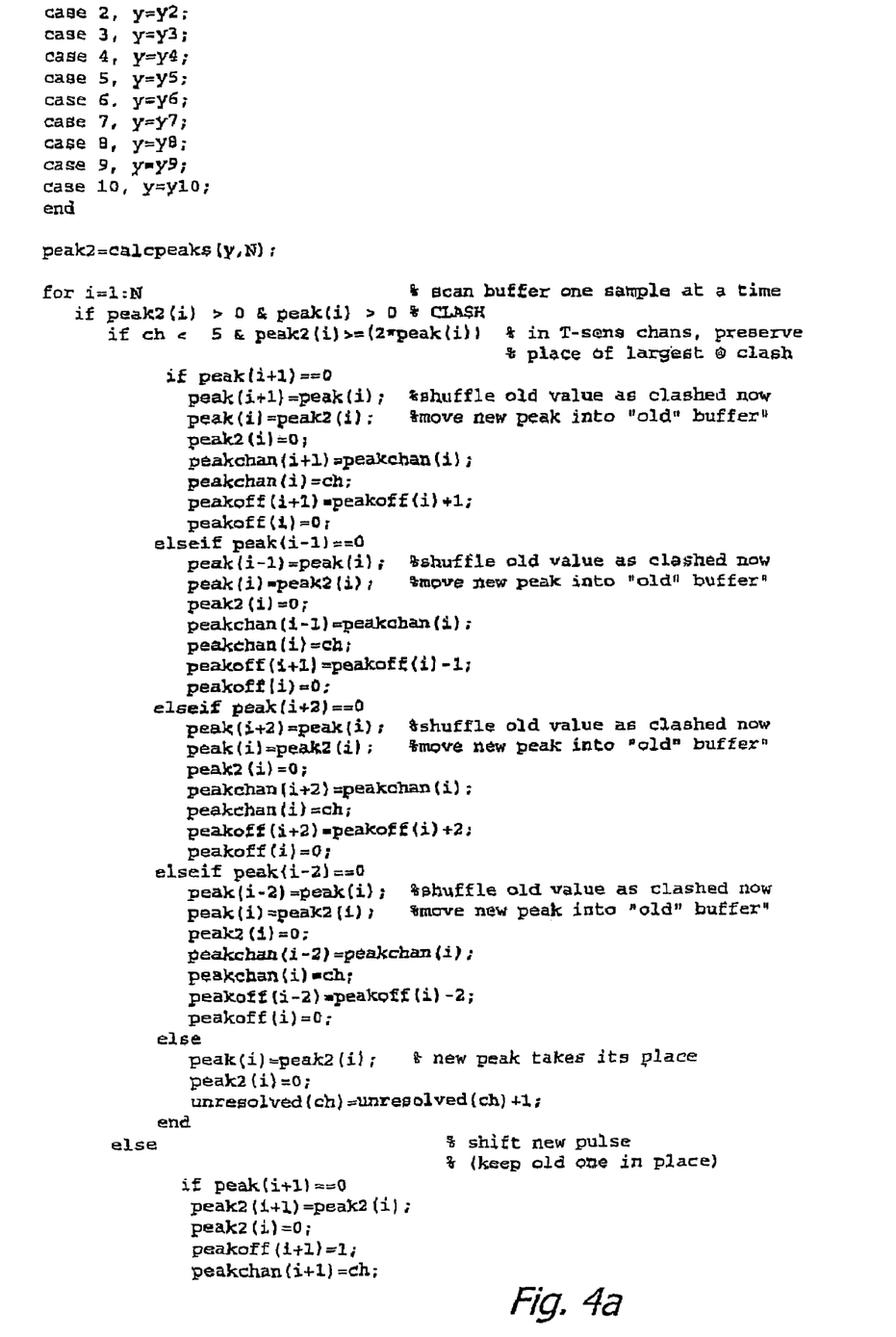
Figure 4B:
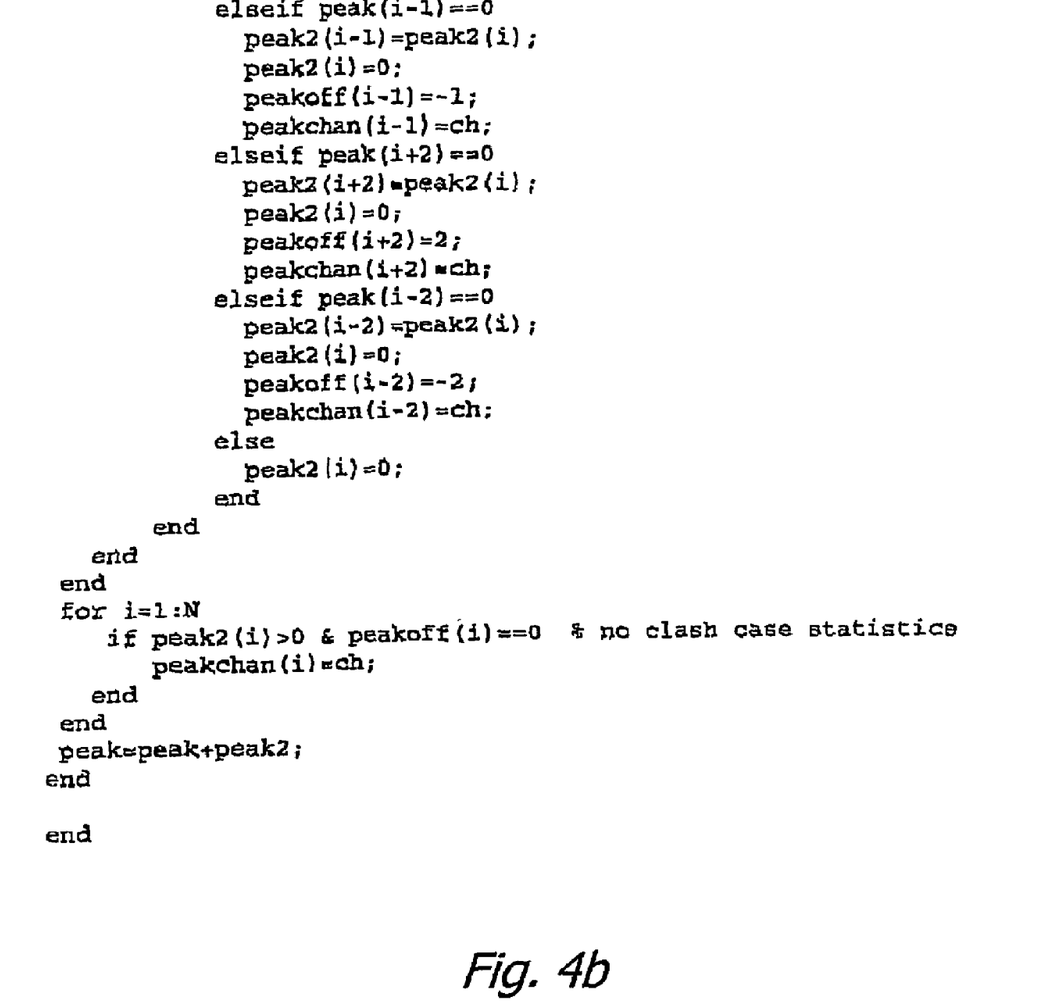

The main code of FIG. 4 then fills a 'total stimulation' buffer by, starting with the lowest frequency channel, adding each channel's peaks into the total buffer, If a clash is encountered, and the time slot requested by the new channel is already filled in the total buffer, the new and old channels are compared for frequency and amplitude according to the following rules. For low frequency bands 1-4 ("channels" in the code) priority is low to high unless the intensity of the higher frequency band peak is at least twice as large as the lower frequency one. The pulse with the higher priority is placed in the "total buffer" at the right time slot. The lower priority one is shuffled along to the nearest free slot, up to 2 time slots to the left or right of the present slot. An alternative, and perhaps more accurate but computationally more expensive approach, when moving the lower priority pulse, is to further compare priority with neighbouring slots rather than just looking for the nearest free slot in which to relocate it.

For channels 5 and higher, since these channels are less important in interaural time delay perception and may contain less accurate temporal information since the peak-proximity limiting criterion will affect high frequencies more than low frequencies, the intensity criterion is excluded and only the frequency priority applies. This avoids high frequency peaks distorting the more important temporal coding of the low frequency peaks, even when the former are larger in amplitude.

Figure 5:
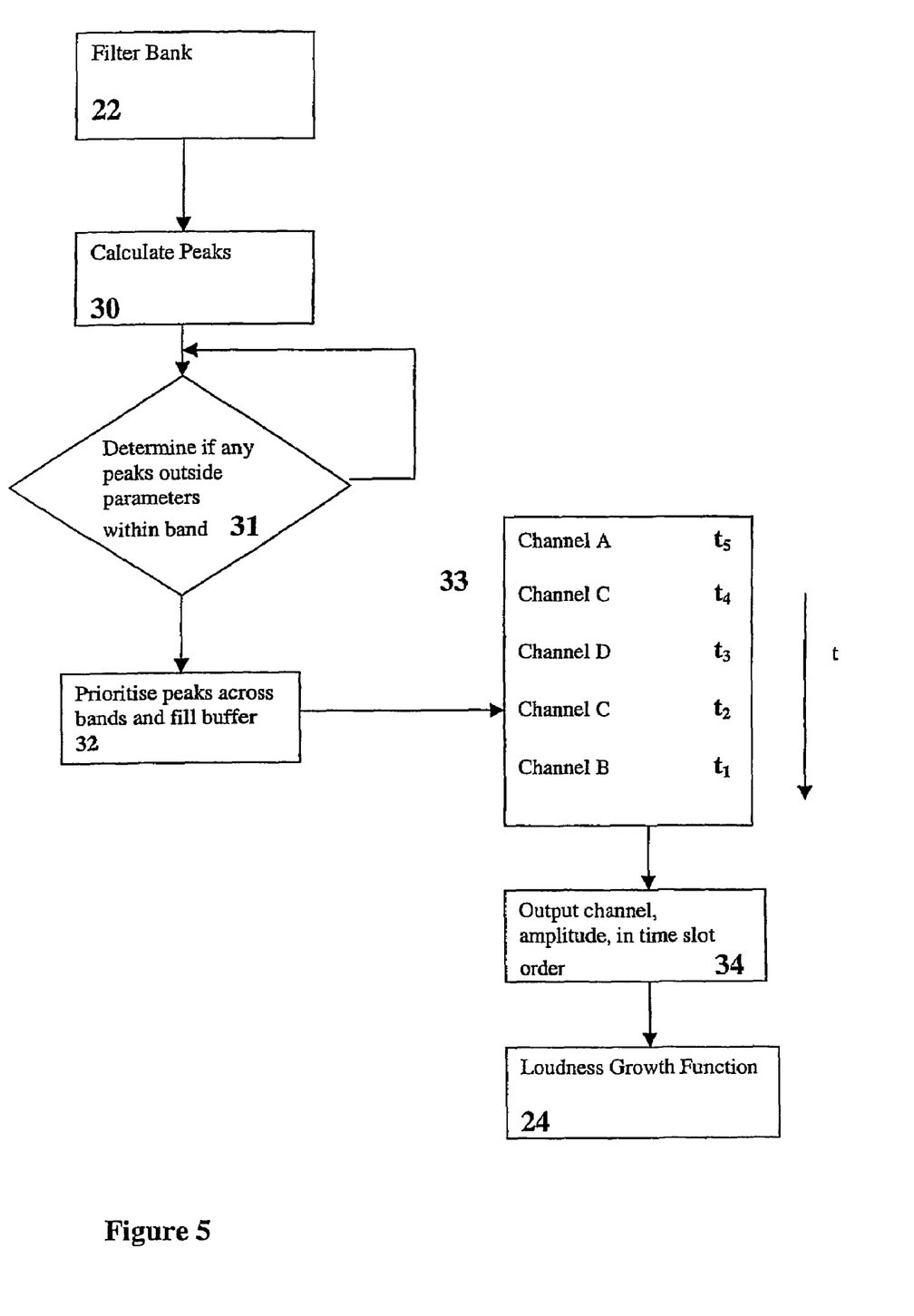
FIG. 5 is a flow chart illustrating schematically process implemented in the code of FIGS. 4 and 5.

FIG. 5 shows in schematic overview the operation of this implementation of the invention. Filterbank 22 outputs a set of signals corresponding to the predefined bands of interest. These signals are then each analysed 30 to detect the peaks in each band, including the time of the peak and its intensity. At 31, the output for each band is analysed to determine whether any of the peaks fall outside the parameters for acceptance. For example, the parameters may include a minimum intensity threshold, or a criteria related to the allowed closeness of peaks in the same band. If one of the peaks is deleted for failing to meet these parameters, the process loops to then recalculate once that peak is deleted.

At 32, the outputs of all the bands are prioritised, according to the criteria described in detail above. On the basis of this priority, the peaks are placed into buffer 33. Each peak is placed into a specific timeslot t1, t2, etc. The timeslots are selected according to the criteria described above. At 34, each peak in the buffer is submitted consecutively to the loudness growth function 24 in time slot order, which further processes the signal as described above.

It should be appreciated that it is also envisaged that a binaural version of this strategy is possible and would involve two independent units with a microphone behind each ear. For optimal bilateral results sampling may need to be synchronised across the two microphone signals in that case. However, when this is not ensured, the error is likely to be less than (1/sample-rate) which is usually in the order of tens of microseconds (at least an order of magnitude smaller than the stimulation time error associated with non synchronised fixed rate or multi-rate bilateral strategies). It is noted that the peak position and coding scheme is only accurate to within one sampling/stimulation interval in any case. The benefit of not synchronising the two sides is that a behind-the-ear (BTE) implementation without connections between the two sides is then feasible.

It will be appreciated that the present invention relates to a broad scheme which can be implemented in various forms. Variations and additions to the basic scheme outlined are possible and expected.

The invention claimed is:

1. A method of generating stimuli for use in a cochlear implant, comprising:
   processing a received audio signal to define signals within a set of frequency channels;
   determining a time and intensity for each of one or more peaks in each of said signals;
   prioritizing each of said peaks according to a predetermined instruction set;
   specifying a minimum time interval between said peaks of each of said signals;
   discarding peaks occurring within said minimum time intervals;
   placing non-discarded peaks, in order of priority, into time slots of a buffer corresponding to the time said non-discarded peaks occur in said signals; and
   outputting from said buffer a set of data for use in generating stimulus instructions.

2. An cochlear implant device, including
   a filter bank configured to receive and process an audio signal to define signals within a set of frequency channels;
   a processing module configured to determine a time and intensity for each of one or more peaks in each of said signals, and configured to prioritize each of said peaks in response to a predetermined instruction set;
   said processing module configured to utilize said instruction set to specify a minimum time interval between said peaks of each of said signals, and to discard peaks occurring within said minimum time intervals;
   a buffer, wherein said processing module is further configured to place non-discarded peaks, in order of priority, into time slots of said buffer corresponding to the time said non-discarded peaks occur in said signals; and
   wherein said device utilizes an output of said buffer to generate stimulus instructions.

3. The method of claim 1, wherein when peaks occur in more than one channel within a sampling period, said method further comprises:
   granting priority to a peaks in a low frequency channel over a peak in a high frequency channel up to a predefined frequency channel, unless said peak in said higher frequency channel has an amplitude which is larger by a predefined amount than said peak in said lower frequency channel;

granting priority to said peaks only on the basis of low frequency channels over high frequency channels for channels higher than said predefined channel; and discarding peaks in said lower priority channels if no appropriate time slot is available for said peaks in said lower priority channel.

4. The method of claim 1, wherein the output data is such that said method further comprises:

presenting stimuli at one or more electrodes in an order which corresponds to the order of corresponding peaks in said audio signal.

5. The method of claim 4, wherein said process further comprises:

presenting said stimuli with a relative timing which substantially corresponds to the timing of said corresponding peaks in said audio signal.

6. A method of generating stimuli for use in a cochlear implant, comprising:

processing a received audio signal to define signals within a set of frequency channels;

determining a time and intensity for each of one or more peaks in each of said signals;

prioritizing said peaks when peaks occur in more than one channel within a sampling period;

granting priority to a peak in a low frequency channel over a peak in a high frequency channel up to a predefined frequency channel, unless said peak in said higher frequency channel has an amplitude which is larger by a predefined amount than said peak in said lower frequency channel;

granting priority to said peaks only on the basis of low frequency channels over high frequency channels for channels higher than said predefined channel;

placing said peaks, in order of priority, into time slots of a buffer corresponding to the time said peaks occur in said signals;

discarding peaks in lower priority channels if no appropriate time slot is available for said peaks in said lower priority channels; and outputting from said buffer a set of data for use in generating stimulus instructions.

7. The method of claim 6, wherein after said peaks have been determined, said method further comprises:

specifying a minimum time interval between said peaks of each of said signals; and discarding peaks occurring within said minimum time intervals.

8. The device of claim 2, wherein when peaks occur on more than one channel within a sampling period, said processing module is further configured to give priority to a peak in a low frequency channel over a peak in a high frequency channel up to a predefined frequency channel, unless said peak in said higher frequency channel has an amplitude which is larger by a predefined amount than said peak in said lower frequency channel;

wherein for frequency channels higher than said predefined channel, said processing module is configured to give priority to peaks only on the basis of low frequency channels over high frequency channels; and wherein if no appropriate time slot is available for a peak in a lower priority channel, said processing module is configured to discard said peak oi said lower priority channel.

9. The device of claim 2, wherein said device is configured to utilize said stimulus instructions to present stimuli at one or more electrodes in an order which corresponds to an order of corresponding peaks of said audio signal.

10. The device of claim 9, wherein said device is further configured to present said stimuli with a relative timing which substantially corresponds to a timing of said corresponding peaks of said audio signal.

11. The method of claim 6, wherein the output data is such that said method further comprises:

presenting stimuli at one or more electrodes in an order which corresponds to the order of corresponding peaks in said audio signal.

12. The method of claim 11, wherein said method further comprises:

presenting said stimuli with a relative timing which substantially corresponds to a timing of said corresponding peaks in said audio signal.

* * * * *

UNITED STATES PATENT AND TRADEMARK OFFICE
CERTIFICATE OF CORRECTION

| | |
|---|---|
| PATENT NO. | : 7,310,558 B2 |
| APPLICATION NO. | : 10/478675 |
| DATED | : December 18, 2007 |
| INVENTOR(S) | : Van H. Richard |

It is certified that error appears in the above-identified patent and that said Letters Patent is hereby corrected as shown below:

On Col. 2, lines 17, 18 and 23 show "multi rate" as two words, should read --multirate--.

Col. 2 Line 62 lists "Otolantyngologica," should read --Otolaryngologica--.

On Col. 3, line 5, "Latyngology" should read --Laryngology--.

On Col. 5, lines 55 and 58 show "multi rate" as two words, should read --multirate--.

On Col. 6, lines 16 and 18 show "multi rate" as two words, should read --multirate--.

Signed and Sealed this

Thirteenth Day of May, 2008

JON W. DUDAS
*Director of the United States Patent and Trademark Office*